United States Patent [19]

Tohzuka et al.

[11] 4,165,340
[45] Aug. 21, 1979

[54] PROCESS FOR PREPARING HEXAFLUOROPROPANONE-2

[75] Inventors: Takashi Tohzuka; Yohnosuke Ohsaka, both of Osaka, Japan

[73] Assignee: Daikin Kogyo Co., Ltd., Osaka, Japan

[21] Appl. No.: 826,248

[22] Filed: Aug. 19, 1977

[30] Foreign Application Priority Data

Aug. 23, 1976 [JP] Japan .................................. 51-100831
May 23, 1977 [JP] Japan .................................. 52-59590

[51] Int. Cl.$^2$ ............................................. C07C 45/04
[52] U.S. Cl. ............................. 260/593 H; 260/597 R
[58] Field of Search ........... 260/593 H, 597 R, 593 R, 260/597

[56] References Cited

U.S. PATENT DOCUMENTS

| | | | |
|---|---|---|---|
| 3,321,515 | 5/1967 | Moore et al. | 260/593 H |
| 3,391,119 | 7/1968 | Anderson | 260/593 H |
| 3,959,367 | 5/1976 | Jeffrey | 260/593 H |
| 4,057,584 | 11/1977 | Takashi et al. | 260/593 H |

*Primary Examiner*—James H. Reamer
*Attorney, Agent, or Firm*—Stevens, Davis, Miller & Mosher

[57] ABSTRACT

A process for preparing hexafluoropropanone-2 from hexafluoropropene by one step reaction which comprises contacting hexafluoropropene and oxygen with a fluorinated alumina or a fluorinated silica-alumina as a catalyst in the presence or absence of water, provided that water is present when the catalyst is the fluorinated alumina.

1 Claim, No Drawings

PROCESS FOR PREPARING HEXAFLUOROPROPANONE-2

The present invention relates to a process for preparing hexafluoropropanone-2. More particularly, it relates to an improved process for preparing hexafluoropropanone-2 from hexafluoropropene with a high efficiency.

Hexafluoropropanone-2 is useful by itself as a catalyst for polymerization of perfluorocyclobutene or triazine. Because of its polymerizability, it forms a terpolymer with tetrafluoroethylene and ethylene. It is also useful as the starting material for the production of bisphenol AF (($C_6H_4$—OH)$_2$C(CF$_3$)$_2$) which is an excellent cross-linking agent for fluorine-containing elastomers.

For production of hexafluoropropanone-2, there is known a method which comprises oxidizing hexafluoropropene and subjecting the resultant 1,2-epoxyhexafluoropropane to rearrangement to obtain hexafluoropropanone-2. For example, hexafluoropropene and oxygen are contacted with activated silica gel at a temperature of 140° to 280° C. to obtain 1,2-epoxyhexafluoropropane, which is then subjected to rearrangement in the presence of a Lewis acid such as aluminum oxide to give hexafluoropropanone-2 (U.S. Pat. No. 3,775,439). Thus, in the conventional method, two steps of reaction are required for the production of hexafluoropropanone-2.

The extensive study revealed that hexafluoropropanone-2 can be prepared from hexafluoropropene and oxygen by one step reaction when a specific catalyst, i.e. fluorinated alumina, is used. Thus, U.S. Ser. No. 695,110, filed June 11, 1976 discloses and claims a process for preparing hexafluoropropanone-2 from hexafluoropropene by one step reaction which comprises contacting hexafluoropropene and oxygen with a fluorinated alumina as a catalyst to give hexafluoropropanone-2.

The subsequent study has revealed that another specific catalyst, i.e. fluorinated silica-alumina, can also accomplish the production of hexafluoropropanone-2 from hexafluoropropene and oxygen in one step reaction.

While the fluorinated alumina and the fluorinated silica-alumina show a good conversion of hexafluoropropene over a long period of time, the selectivity to hexafluoropropanone-2 is lowered with the lapse of time so that the yield of hexafluoropropanone-2 is decreased with increase of the production of undesirable by-products.

The further study has revealed that the presence of water in the reaction system overcomes such drawback and can maintain an excellent selectivity to hexafluoropropanone-2 for a long period of time without deterioration of the conversion of hexafluoropropene.

According to the present invention, there is provided a process for preparing hexafluoropropanone-2 from hexafluoropropene by one step reaction which comprises contacting hexafluoropropene and oxygen with a fluorinated alumina or a fluorinated silica-alumina as a catalyst in the presence or absence of water, provided that water is present when the catalyst is the fluorinated alumina.

The catalyst to be used in the process of this invention is a fluorinated alumina or a fluorinated silica-alumina.

As the fluorinated alumina, there may be used any material known as "fluorinated alumina". Some of the fluorinated alumina are known as catalysts in reforming of hydrocarbons, and some others are known as catalysts in rearrangement of chlorofluorohydrocarbons. The fluorinated alumina comprises aluminum, fluorine and oxygen, and its fluorine content is desired to be from about 0.5 to 50% by weight.

The fluorinated alumina as the catalyst is ordinarily prepared by treatment of alumina with a fluorinating agent. As the alumina, there can be employed, without particular limitation, any conventional one such as natural alumina or synthetic alumina. Particularly preferred are activated alumina such as highly porous alumina obtained by calcining $\alpha$-alumina hydrate or $\beta$-alumina hydrate under appropriately controlled conditions. Some of commercially available activated alumina contains silica as the component for tablet-formation, and the one having a silica content of not more than about 20% by weight may be taken in the category of the term "alumina" as herein used.

As the fluorinating agent, there may be used an inorganic fluorinating agent or an organic fluorinating agent. Examples of the inorganic fluorinating agent are hydrogen fluoride, silicon tetrafluoride, sulfur fluoride (e.g. sulfur tetrafluoride, sulfur hexafluoride), sulfuryl fluoride, thionyl fluoride, ammonium fluoride (e.g. acidic ammonium fluoride, neutral ammonium fluoride), etc. Examples of the organic fluorinating agent include fluorohydrocarbons, chlorofluorohydrocarbons, bromofluorohydrocarbons, etc. Fluorine-containing compounds of the formula: $C_nF_aH_bX$ wherein X is an oxygen atom or a nitrogen atom, n is an integer of 1 to 8 (preferably 1 to 4), a is an integer of 1 to 2n+m, b is an integer of 0 to 2n+m−1 and m is an integer of 2 when X is an oxygen atom or an integer of 3 when X is a nitrogen atom, as disclosed in Japanese Patent Publication (unexamined) No. 1578/1972, can be also used as the organic fluorinating agent. The fluorohydrocarbons may be saturated or unsaturated hydrocarbons having not more than 8, preferably not more than 4, carbon atoms in which at least one hydrogen atom is substituted with a fluorine atom. A higher degree of substitution with fluorine atoms is more preferable. Specific examples are $CF_4$, $CHF_3$, $CF_3CF_3$, $CHF_2CF_3$, $CHF_2CHF_2$, $CH_3CF_3$, $CH_2FCHF_2$, $CH_2=CF_2$, $CF_3CF=CF_2$, $CF_2=CF_2$, etc. The chlorofluorohydrocarbons and the bromofluorohydrocarbons may be saturated or unsaturated hydrocarbons having not more than 8, preferably not more than 4, carbon atoms in which hydrogen atoms are substituted with at least one fluorine atom and at least one chlorine or bromine atom and include specifically $CCl_3F$, $CCl_2F_2$, $CHCl_2F$, $CHClF_2$, $CClF_2CCl_2F$, $CCl_3CF_3$, $CCl_2FCCl_2F$, $CCl_3CCl_2F$, $CClF_2CClF_2$, $CCl_2FCF_3$, $CF_3CCl=CClCF_3$, $CF_2BrCFClBr$, $CF_2BrCHClF$, $CF_2BrCF_2Br$, etc. Examples of the fluorine-containing compounds are hexafluoroacetone, hexafluoro-1,2-epoxyethane, decafluorodiethyl ether, tri(trifluoromethyl)amine, tetrafluoroethyl methyl ether, etc. Among them, perfluoroalkanes such as tetrafluoromethane and perfluoroalkenes such as hexafluoropropene are particularly preferred.

The preparation of the catalyst may be carried out by various procedures depending on the kind of the fluorinating agent as employed.

When, for instance, hydrogen fluoride or ammonium fluoride is employed as the fluorinating agent, the activated alumina is contacted with it at a temperature of about 20° to 450° C. so as to give the fluorinated alumina. When sulfur fluoride, sulfuryl fluoride or thionyl fluoride is employed, the activated alumina may be contacted with the fluorinating agent at a temperature of about 300° to 500° C. to give the fluorinated alumina. In some cases, sulfurous compounds may be formed and deposited on the catalyst, but they are not poisonous to the catalytic activity.

When the fluorinating agent is an organic fluorinating agent, the activated alumina may be contacted with it at a temperature of about 100° to 600° C., preferably of about 150° to 450° C. to give the desired fluorinated alumina.

In case of using an organic fluorinating agent, the treatment of the activated alumina with a chlorohydrocarbon or a bromohydrocarbon may be effected prior to the contact with the organic fluorinating agent. The coexistence of a chlorohydrocarbon or a bromohydrocarbon on the contact of the activated alumina with the organic fluorinating agent is sometimes recommendable, since the fluorination of the activated alumina can be accomplished more smoothly under a lower temperature.

As the chlorohydrocarbon or the bromohydrocarbon, there may be employed a saturated or unsaturated hydrocarbon having not more than 8, preferably not more than 4, carbon atoms in which at least one hydrogen atom is substituted with a chlorine or bromine atom. A higher degree of substitution with chlorine or bromine atoms is more preferable. Substitution with chlorine or beomine atoms alone or with both of them is admissible. Specific examples are $CCl_4$, $CHCl_3$, $CCl_3CCl_3$, $CHCl_2CCl_3$, $CCl_2=CCl_2$, $CHCl=CCl_2$, $CHBr_3$, $CCl_2Br_2$, etc. Among them, perchlorohydrocarbons are particularly preferred.

Explaining the preparation of the fluorinated alumina by treatment of the activated alumina with the fluorohydrocarbon and the chlorohydrocarbon or the bromohydrocarbon, the activated alumina may be contacted first with the chlorohydrocarbon or the bromohydrocarbon at a temperature of about 100° to 400° C. (preferably 100° to 200° C.) and then with the fluorohydrocarbon at a temperature of about 100° to 400° C. (preferably 100° to 350° C.), whereby the fluorinated alumina can be obtained.

Alternatively, the activated alumina may be contacted with a mixture of the chlorohydrocarbon or the bromohydrocarbon and the fluorohydrocarbon at a temperature of about 100° to 400° C. (preferably 200° to 300° C.). The mixing proportion of the chlorohydrocarbon or the bromohydrocarbon to the fluorohydrocarbon is determined depending on their kinds. In the combination of tetrachloromethane and trichlorotrifluoroethane, for instance, the molar ratio of tetrachloromethane and trichlorotrifluoroethane is desired to be about 0.1–5:1.

In addition to the procedures as above, the fluorinated alumina may be produced by any conventional procedure, for instance, as described in Japanese Patent Publications Nos. 11605/1964 and 27748/1968.

The fluorinated silica-alumina comprises aluminum, silicon, fluorine and oxygen as the essential components, and the desirable fluorine content is from about 0.5 to 50% by weight.

The fluorinated silica-alumina may be prepared by treatment of silica-alumina with a fluorinating agent in the substantially same manner as adopted in the preparation of the fluorinated alumina. As the fluorinating agent, there may be employed the one as mentioned above in connection with the preparation of the fluorinated alumina. The starting silica-alumina is per se well known and may be the one having a silica content of more than about 20% by weight. Usually, the proportion of silica and alumina in the silica-alumina is from about 25:75 to 90:10 by weight. A preferred proportion of silica and alumina is from about 30:70 to 80:20.

The process of the invention can be effected by contacting hexafluoropropene and oxygen with the catalyst in a per se conventional manner. Thus, hexafluoropropene and oxygen may be contacted with a fixed bed, moving bed or fluidized bed of the catalyst in an appropriate reaction vessel or tube in a continuous system or a closed system.

The mixing proportion of hexafluoropropene and oxygen is usually about 1:10–0.1 (molar ratio), preferably about 1:2–0.3. When the amount of oxygen is smaller than the lower limit of the said range, the conversion rate is low. When the amount of oxygen is larger than the upper limit, the efficiency of apparatus is reduced. In case of necessity, an inactive gas such as carbon dioxide, nitrogen or helium may be employed as the diluent.

As stated above, the presence of water in the reaction system is preferred to maintain a high selectivity of hexafluoropropene to hexafluoropropanone-2 for a long period of time. The introduction of water to the reaction system may be effected at any stage of the contact, e.g. from the initial stage of the contact or in the course of the contact. Further, it may be carried out continuously or discontinuously. The amount of water to be present in the reaction system may be usually not less than about 0.001 mol, preferably from about 0.001 to 0.03 mol, per 1 mol of hexafluoropropene.

The reaction temperature at the contact is usually from about 80° to 300° C., preferably from about 100° to 250° C. When the temperature is lower than the lower limit of the said range, the conversion rate is lowered. When the temperature is higher than the upper limit, the yield is reduced. At a temperature lower than about 80° C., the reaction hardly proceeds. At a temperature higher than about 300° C., the yield is extremely low. The reaction pressure may be an atmospheric pressure or a higher pressure. In general, a higher pressure is preferable for increasing the conversion rate and the yield. For industrial use, a pressure of about 0 to 20 $kg/cm^2G$ is usually adopted.

The contact time is determined on the other conditions, particularly temperature. At a higher temperature, a shorter contact time is adopted, and at a lower temperature, a longer cOntact time is desired, as in case of other usual reactions. In general, a contact time of 30 minutes or less (e.g. 0.5 second) is preferable. A longer contact time results in a higher conversion. From the economical viewpoint, a proper contact time may be chosen. For instance, a contact time of about 1 second to 10 minutes is usually adopted in a continuous system in which the temperature is about 100° to 250° C.

When the catalyst is used for a long period of time, carbonaceous materials are deposited on its surface to lower the catalytic activity. In such case, the catalytic activity can be recovered by heating the catalyst in the presence of oxygen or an oxygen-containing material such as air at a temperature of about 350° to 500° C.

While a high conversion of hexafluoropropene can be maintained for a relatively long period of time, the selectivity to hexafluoropropanone-2 is gradually lowered with the increase of the production of by-products.

Lowering of the selectivity to hexafluoropropanone-2 is, however, prevented remarkably when water is present in the reaction system, and the life of the catalyst can be prolonged several times. Further, the catalyst once deteriorated in the selectivity to hexafluoropropanone-2 can be reactivated by contacting with water.

As already mentioned, the production of hexafluoropropanone-2 from hexafluoropropene has been hitherto effected by two steps of reaction. According to the process of this invention, the production can be effected more efficiently by only one step of reaction. On analyzing the reaction products, formation of 1,2-epoxyhexafluoropropane, which is the intermediate in the conventional process, is not confirmed. In the conventional process, the second step of reaction is usually carried out in the presence of a Lewis acid as the catalyst.

While the conventionally known oxidation catalyst (e.g. silica) for hexafluoropropene mainly produces 1,2-epoxyhexafluoropropane, it is revealed that the fluorinated alumina does not produce 1,2-epoxyhexafluoropropane. On the other hand, Lewis acids (e.g. alumina, aluminum trichloride) known as catalysts for rearrangement of 1,2-epoxyhexafluoropropane to hexafluoropropanone-2 do not exert any activity for the reaction of hexafluoropropene with oxygen. From these facts, the fluorinated alumina is presumed to result in the selective formation of hexafluoropropanone-2 in the oxidation of hexafluoropropene by its unexpected characteristics.

Practical and presently preferred embodiments of the invention are illustratively shown in the following Examples.

EXAMPLE 1

(1) Preparation of fluorinated alumina:

In a Pyrex glass made reaction tube (28 mm in inner diameter; 1000 mm in length) set up vertically in an electric furnace, granular activated alumina having a particle size of 2.3–4.7 mm ("Neobead C-4" manufactured by Mizusawa Kagaku; alumina gel) (50 g) is charged, and the temperature is elevated to 350° to 370° C. in nitrogen stream. Sulfur hexafluoride is introduced therein with a rate of 200 ml/min (25° C., 1 atmospheric pressure) at the same temperature for 9 hours. The thus produced fluorinated alumina contains 12.3% by weight of fluorine.

(2) Preparation of hexafluoropropanone-2:

In a Hastelloy C made reaction tube (18 mm in inner diameter; 1000 mm in length), the catalyst obtained in (1) (40 g) is charged, and a mixture of hexafluoropropene and oxygen (2:1 in molar ratio) is introduced therein under the following conditions: temperature, 175° C.; pressure, 1 atmospheric pressure; supplying rate of the mixture, 90 ml/min (25° C., 1 atmospheric pressure). During the reaction, water is introduced into the reaction system as shown in Table 1-1. The produced gas from the reaction tube is subjected to gas chromatographic analysis for determination of the conversion of hexafluoropropene and the yield of hexafluoropropanone-2. The results are shown in Table 1-2.

Table 1-1

| Period of time after initiation of reaction (hrs) | Amount of water introduced (mol per 1 mol of hexafluoropropene) |
|---|---|
| 0–160 | 0 |
| 160–170 | 0.016 |

Table 1-1-continued

| Period of time after initiation of reaction (hrs) | Amount of water introduced (mol per 1 mol of hexafluoropropene) |
|---|---|
| 170–260 | 0 |
| 260–270 | 0.008 |

Table 1-2

| Time after initiation of reaction (hrs) | | Conversion (mol %) | Yield (mol %) |
|---|---|---|---|
| 50 | | 14.8 | 66.8 |
| 160 | (immediately before first introduction of water) | 34.4 | 29.8 |
| 165 | (with introduction of water) | 14.6 | 71.5 |
| 260 | (immediately before second introduction of water) | 20.2 | 35.8 |
| 265 | (with introduction of water) | 15.1 | 71.6 |
| 450 | (with introduction of water) | 15.4 | 70.4 |

From Table 1-2, it is obvious that, though the yield of the objective hexafluoropropanone-2 is markedly decreased after about 150 hours from the initiation of the reaction, it is recovered by the introduction of water, and even after completion of the introduction of water, a good yield can be maintained for a considerably long period of time.

EXAMPLE 2

Hexafluoropropanone-2 is prepared in the same manner as in Example 1 but effecting the introduction of water as shown in Table 2-1. The results are shown in Table 2-2.

Table 2-1

| Period of time after initiation of reaction (hrs) | Amount of water introduced (mol per 1 mol of hexafluoropropene) |
|---|---|
| 0–160 | 0 |
| 160–360 | 0.003 |

Table 2-2

| Time after initiation of reaction (hrs) | | Conversion (mol %) | Yield (mol %) |
|---|---|---|---|
| 165 | (immediately after introduction of water) | 14.8 | 66.9 |
| 350 | (with introduction of water) | 14.9 | 67.1 |

EXAMPLE 3

Hexafluoropropanone-2 is prepared in the same manner as in Example 1 but effecting the introduction of water continuously in an amount of 0.001 mol per 1 mol of hexafluoropropene from the initiation of the reaction.

The conversion of hexafluoropropene after 265 hours from the initiation of the reaction is 15.0 mol %, and the yield of hexafluoropropanone-2 at that time is 69.3 mol %.

EXAMPLE 4

(1) Preparation of fluorinated silica-alumina:

In a Pyrex glass made reaction tube (22 mm in inner diameter; 1000 mm in length), granular silica-alumina ($SiO_2$:$Al_2O_3$= 60:40 by weight) having a particle size of 2–4 mm (35 g) is charged, and the temperature is elevated to 400° C. in nitrogen stream and this temperature is maintained for 2 hours for dehydration. The temperature is lowered to 200° C., and $CCl_2F_2$ gas is introduced into the reaction tube in place of nitrogen with a rate of 50 ml/min at the same temperature for 4 hours. Then, oxygen gas is introduced therein at 300° C. for 1 hour. The thus obtained fluorinated silica-alumina contains 3.2% by weight of fluorine.

(2) Preparation of hexafluoropropanone-2:

A bed of the catalyst obtained in (1) charged in the reaction tube as used in (1) is heated at 160° C., and hexafluoropropene and oxygen are passed through respectively with rates of 50 ml/min and 30 ml/min under a total pressure of 1 atmospheric pressure, during which water is continuously introduced therein in an amount of 0.001 mol per 1 mol of hexafluoropropene. After 3 and 265 hours, the produced gas is subjected to gas chromatographic analysis, and it is confirmed that the conversion of hexafluoropropene is respectively 9.8 and 10.5 mol %, and the yield of hexafluoropropanone-2 is respectively 68.4 and 67.9 mol %.

EXAMPLE 5

A bed of the catalyst obtained in Example 4 (1) charged in the reaction tube as used in Example 4 (1) is heated at 160° C., and hexafluoropropene and oxygen are passed through respectively with rates of 50 ml/min and 30 ml/min under a total pressure of 1 atmospheric pressure. After 3 hours, the produced gas is subjected to gas chromatographic analysis, and it is confirmed that the conversion of hexafluoropropene is 10.0 mol %, and the yield of hexafluoropropanone-2 is 68.8 mol %.

Treatment of hexafluoropropene and oxygen with silica-alumina in the same manner as above but heating at 200° C. and passing through for 15 hours is carried out. As the result, a trace of carbon dioxide gas is produced, and no material conversion of hexafluoropropene is observed.

What is claimed is:

1. A process for preparing hexafluoropropanone by a one step reaction which comprises contacting hexafluoropropene and oxygen in a molar ratio of 1:10–0.1 at a temperature from about 80° to 300° C. and in the presence of water in an amount of from about 0.001 to 0.03 mole per mole of hexafluoropropene, with
   (a) a fluorinated alumina catalyst, having a fluorine content from about 0.5 to 50% by weight, or
   (b) a fluorinated silica-alumina catalyst having a fluorine content from about 0.5 to 50% by weight.

* * * * *